United States Patent
Haffner et al.

(10) Patent No.: US 7,304,721 B2
(45) Date of Patent: Dec. 4, 2007

(54) METHOD FOR DYNAMICALLY MONITORING A RETICLE

(75) Inventors: Henning Haffner, Pawling, NY (US); Karin Eggers, Dresden (DE); Norbert Haase, Dresden (DE); Andreas Frangen, Dresden (DE); Carmen Jaehnert, Dresden (DE)

(73) Assignee: Infineon Technologies AG, Neubiberg (DE)

( * ) Notice: Subject to any disclaimer, the term of this patent is extended or adjusted under 35 U.S.C. 154(b) by 395 days.

(21) Appl. No.: 10/984,797

(22) Filed: Nov. 10, 2004

(65) Prior Publication Data
US 2005/0125164 A1 Jun. 9, 2005

(30) Foreign Application Priority Data
Nov. 11, 2003 (DE) ............................ 103 52 639

(51) Int. Cl.
*G01N 21/00* (2006.01)
(52) U.S. Cl. .................. 356/72; 356/239.1; 356/237.4; 356/237.5; 716/4
(58) Field of Classification Search ............ 250/492.2, 250/559.3, 559.29; 356/401, 239.1, 237.1–237; 702/35; 355/53, 55; 430/5, 4, 30; 716/4, 716/19–21
See application file for complete search history.

(56) References Cited

U.S. PATENT DOCUMENTS

| 5,323,440 | A | 6/1994 | Hara et al. | |
|---|---|---|---|---|
| 6,433,351 | B1* | 8/2002 | Yonekawa | 250/559.3 |
| 6,703,170 | B1* | 3/2004 | Pindo | 430/5 |

OTHER PUBLICATIONS

Grenville, A. et al., "Behavior of Candidate Organic Pellicle Materials Under 157nm Laser Irradiation," 10 pages.
Bhattacharyya, K. et al., "The Case of the "Growing" Reticle Defect at 193-nm Lithogrphy," Yield Management Solutions, Summer 2003, pp. 78-84.

* cited by examiner

*Primary Examiner*—Layla G. Lauchman
(74) *Attorney, Agent, or Firm*—Edell, Shapiro & Finnan, LLC

(57) ABSTRACT

The method of dynamically monitoring a reticle includes preventively macro monitoring and defect inspecting with regard to mechanical loading, including particle deposits or electrostatically induced damage, and energy load, including the associated changes to the reticle material and surface characteristics. Different surface distributions of the absorber layer as well as characteristics of the exposure system, such as $N_2$ purging of the projection lens/reticle area in order to reduce contamination and recrystallization on optically active surfaces are considered.

12 Claims, 1 Drawing Sheet

METHOD FOR DYNAMICALLY MONITORING A RETICLE

CROSS REFERENCE TO RELATED APPLICATIONS

This application claims priority under 35 USC §119 to German Application No. DE 10352639.0, filed on Nov. 11, 2003, and titled "Method for Dynamic Monitoring of a Reticle," the entire contents of which are hereby incorporated by reference.

FIELD OF THE INVENTION

The invention relates to a method for dynamically monitoring of a reticle, which is used for the photolithographic structuring of a semiconductor wafer in a projection apparatus.

BACKGROUND

In order to produce integrated circuits, layers with different electrical characteristics are normally applied to semiconductor wafers, and are structured lithographically. A lithographic structuring step may include applying a photosensitive resist, exposing and developing of the resist with a predetermined structure for the relevant plane, and transferring the resist mask to the layer underneath in an etching step.

A scanner or stepper is normally used as the exposure apparatus for the lithographic projection step for a circuit pattern. In the exposure apparatus, the photosensitive resist is exposed to electromagnetic radiation at a predetermined wavelength, which, for example, is in the UV band. The exposure dose produced by the exposure of the resist at the location of the semiconductor wafer is chosen in accordance with the specifications for the resist layer. The mean dose required for structure mapping is typically approximately 30 $mJ/cm^2$.

Each individual layer of the circuit pattern is normally mapped onto the semiconductor wafer by a mask (or reticle) and projection optics. The reticle includes a substrate layer, which is provided with absorbent elements, such as a chromium layer, which model the circuit pattern. The reticle is generally provided with a protective film, i.e., the pellicle. The pellicle is used to protect the structure face against deposits. The projection optics in the exposure apparatus frequently result in a reduction of the circuit pattern during the transfer to the resist.

The semiconductor wafer is generally placed on a substrate holder and is moved to an appropriate position for exposure. The circuit pattern arranged on a mask is then successively transferred to individual exposure fields on the photosensitive resist. The size of an exposure field is normally about 25 mm×35 mm.

The reticles, which are used in the lithographic exposure process, are subject to mechanical loads, which may cause defects or contamination, as a result of the movements within and outside the exposure systems.

Furthermore, particles and contamination may become attached to the surface by adhesion from the surrounding atmosphere, so that the reticles must be monitored within predetermined time intervals, but at least before use after a lengthy pause in use.

In order to allow such monitoring to be carried out in a large-volume manufacturing process and with a wide range of products, the number of reticle movements are generally counted automatically. In this case, the number of movements of the reticle within and outside the exposure apparatuses, for example, with respect to a storage location, are normally counted, and a monitoring limit is derived from this value. Furthermore, a rigid time schedule is predetermined, determining a further monitoring limit as a function of the period of use. Reticle monitoring is then carried out upon reaching the rigid monitoring limits, during which process macro inspections or defect inspections are carried out.

Macro inspections are large-area oblique light inspections in white light in order to identify defect locations or particles above a size of about 10 µm in scattered light. In order to identify smaller defects, other methods are used, for example, laser beam scanning methods, scatterometry, or reverse image identification with layer comparison.

One problem which has not been observed much until now in this context is that the monitoring limits are defined independently of the actual radiation load on the reticle. As a result of the structure transfer of the structures on the reticle to the semiconductor wafer through reduction optics of electromagnetic radiation, the reticle is subject to a not inconsiderable radiation load, which leads to damage and contamination as a result of energy absorption and photochemical processes in the various layers of the reticle material. A rigid monitoring system ignores the fact that observed recrystallization on the reticle front face and rear face as well as pellicle cloudiness, which may occur, may be initiated by the influence of electromagnetic radiation.

Thus, for example, the presence of ammonium ions and carbon dioxide on the reticle surface leads to the formation of tricyanic acid crystals or ammonium and sulfate ions in order to form ammonium sulfate, both of which can grow when illuminated with energy, depending on the wavelength. The presence of ammonium ions and carbon dioxide leads to the formation of ammonium acid crystals on the reticle surface, which may grow when illuminated with energy, depending on the wavelengths.

SUMMARY

A method for dynamically monitoring a reticle includes monitoring the reticle without rigid monitoring limits. The dose value of the electromagnetic radiation at the location of the layer is determined for each exposure. The characteristics of the projection lens of the projection apparatus for the predetermined wavelength are recorded for each exposure. The clear field ratio of the reticle is determined. The illuminated area of the semiconductor wafer is determined. The radiant transmittance of the pellicle for the predetermined wavelength is determined. The radiant transmittance of the absorber layer for the predetermined wavelength is determined. The radiant transmittance of the reticle substrate for the predetermined wavelength is determined. The maximum number of wafer exposures is calculated from the monitoring value, from the dose value, from the characteristics of the projection lens, from the clear field ratio, from the illuminated area, from the radiant transmittance of the pellicle, from the radiant transmittance of the absorber layer, and from the radiant transmittance of the reticle substrate, while the reticle is monitored.

In the method according to the invention, reticles are preventively monitored with regard to mechanical loading, including particle deposits or electrostatically induced damage, and energy load, including the changes to the reticle material and surface characteristics associated with this.

Different surface distributions of the absorber layer as well as characteristics of the exposure system are considered.

In one embodiment of the method, the maximum number of wafer exposures for the reticle substrate and for the absorber layer of the reticle are determined separately, and the reticle monitoring is determined from the lower of the two values.

According to this procedure, different characteristics of the reticle substrate and of the absorber layer of the reticle, which may result, for example, from different surfaces can be taken into account.

In another embodiment of the method, a correction factor is applied to locally different clear field ratios at different positions of the reticle. According to this procedure, circuit patterns with highly fluctuating clear field ratios can be corrected appropriately without having to monitor the reticle too frequently or too rarely.

In another embodiment of the method, the maximum number of wafer exposures in the presence of measures, which prevent contamination is calculated using a further correction factor. According to this procedure, for example, the influence of nitrogen purging in the projection lens/reticle area, which extends the monitoring intervals, can be considered.

BRIEF DESCRIPTION OF THE DRAWINGS

The invention will now be explained in more detail with reference to the attached drawings, in which.

DETAILED DESCRIPTION

Figure 1:
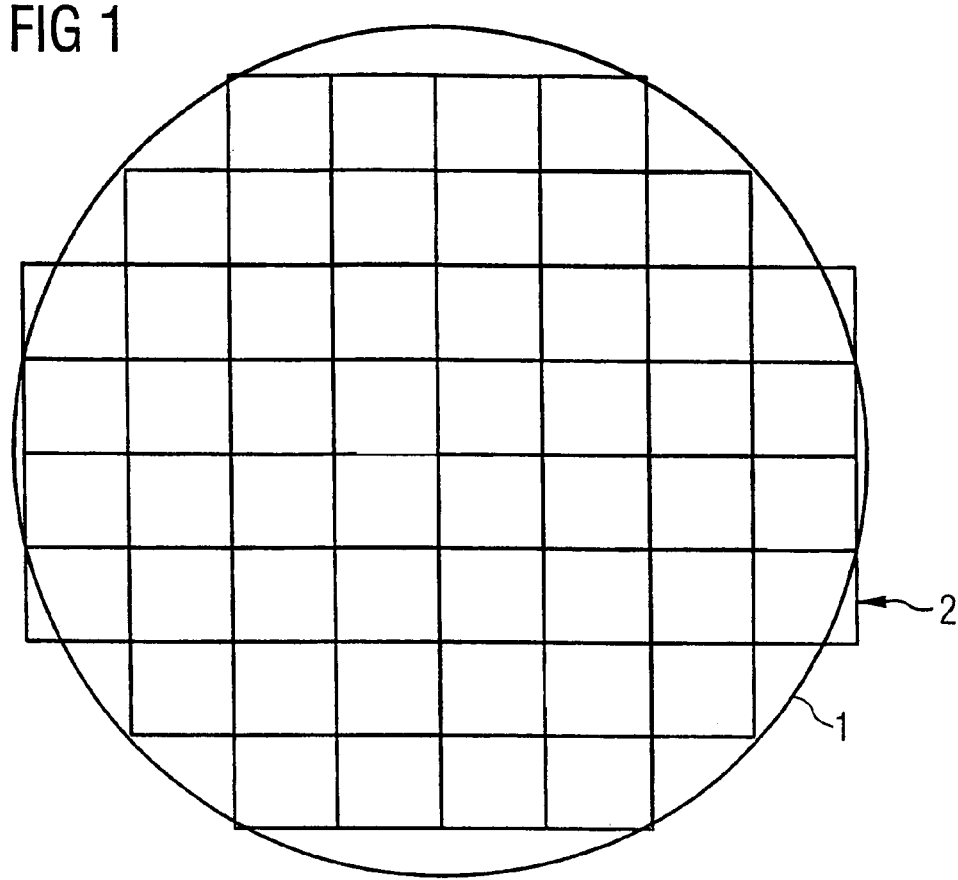
FIG. 1 shows, schematically, a plan view of a semiconductor wafer which is exposed with exposure fields according to the method according to the invention.

FIG. 1 shows a semiconductor wafer 1 which is exposed by an exposure appliance, for example, a scanner or a stepper, in individual exposure fields 2. A semiconductor wafer 1 with a diameter of 300 mm results in a typical value of about 100 exposed image fields 2, in which case the maximum size of an image field may be about 25 mm×35 mm. The image field to be exposed is also referred to as the shot.

Figure 2:
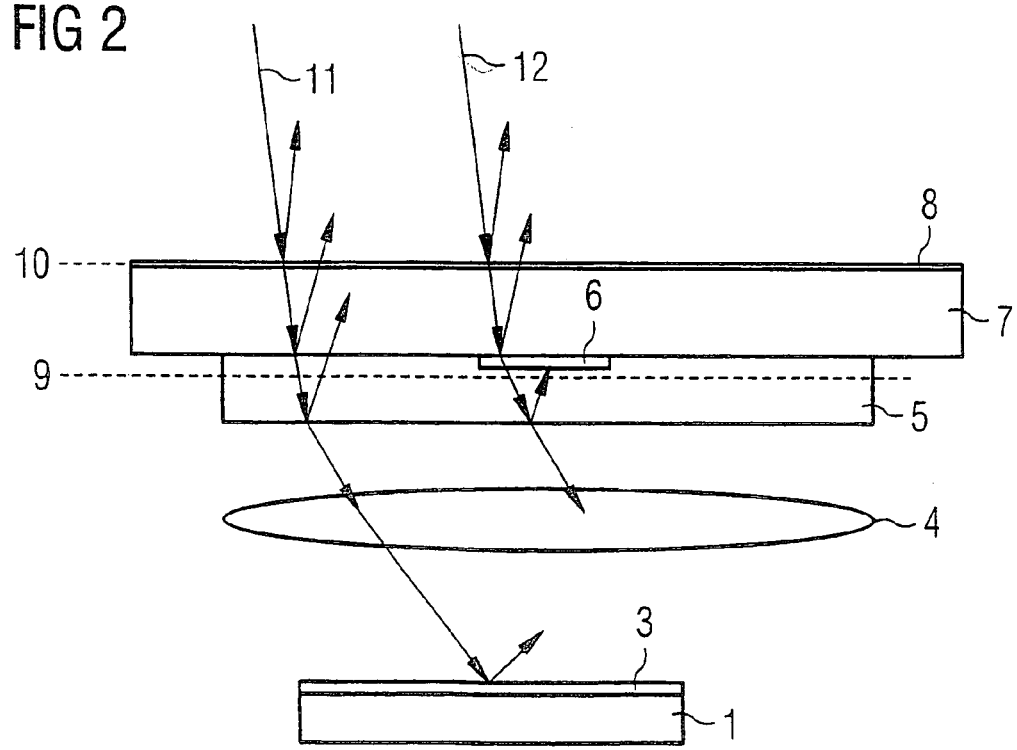
FIG. 2 shows, schematically, a side view of an exposure apparatus in which the method according to the invention can be used.

FIG. 2 shows, schematically, an exposure apparatus with an projection lens 4, which is used for lithographic structure transfer of a circuit pattern of a reticle to a resist layer 3 on the semiconductor wafer 1. The projection lens 4 is between the reticle and the semiconductor wafer 1. The reticle may include a reticle substrate 7, an absorber layer 6, a pellicle 5 which covers the front face 9 of the reticle and, optionally, an antireflection layer 8 applied to the rear face 10 of the reticle. The absorber layer 6 is applied to the front face 9 of the reticle, and is structured in accordance with the circuit pattern. The absorber layer 6 may, for example, be a chromium layer or, in the case of a half-tone phase mask, an MoSi layer. The reticle substrate 7 may include, for example, of quartz glass, with a thin polymer film normally being used for production of the pellicle 5.

The measured dose value $E_{wafer}$ at the location of the resist layer 3 is the point of origin for the analyses of the energy load on the front face 9 and rear face 10 of the reticle. FIG. 2 shows two beam paths, with an exposure as far as the resist layer taking place in the first beam path 11, while the electromagnetic radiation in the second beam path 12 is absorbed in the projection lens 4. The dose value $E_{wafer}$ of a lithographic exposure system is a dynamic control variable and can be monitored over the measured width of structure elements of the exposed resist layer 3. Against this background, a dose value $E_{reticle}$ underneath the reticle location as seen from the semiconductor wafer, can be taken into account for the characteristics of the imaging optics. Since the dose value $E_{wafer}$ at the wafer location is a control variable in an exposure system, the radiation dose at the location of the reticle can be used to calculate the miniaturization scale M, projection lens transmission $T_{projection\ lens}$ and imaging field size of the steppers/scanners used, taking into account the optical characteristics of the exposure system.

A clear field ratio (CFR) for the area of the reticle, which is illuminated by the exposure system, can be determined from the layout of the circuit pattern. The bright field coverage level of the circuit pattern is determined for this purpose, in order to find the proportion of the incident electromagnetic radiation which passes through the reticle and that which is absorbed by the absorber layer. In order to take account of any significant asymmetries in the light/dark area distribution within the circuit pattern, the value of the clear field ratio CFR may be corrected, if required, by forming a mean value from locally determined values for the clear field ratio CFR of the reticle. The radiation dose in the vicinity of the absorber layer 5 can be defined, taking into account the bright field coverage level CFR, the radiant transmittance $T_{pellicle}$ of the pellicle 5 which is located on the reticle, and the radiant transmittance $T_{absorber}$ of the absorber layer 6 of the reticle, as:

$$E_{absorber} = Z_{wafer\_absorber} * E_{wafer} * S_{wafer} * T_{pellicle} * [CFR + (1-CFR)*T_{absorber}]^2/(M^2 * T_{projection\ lens})$$

Where $Z_{wafer\_absorber}$ is the number of exposed wafers.

Taking account of the material dispersion of the substrate, using $Z_{wafer\_substrate}$ for the number of exposed semiconductor wafers, the following expression is obtained analogously for the radiation dose on the substrate rear face:

$$E_{substrate} = Z_{wafer\_substrate} * E_{wafer} * S_{wafer} * T_{pellicle} * [CFR+(1-CFR)*T_{absorber}]/(T_{substrate}*M^2*T_{projection\ lens}).$$

If those dose values for $E_{absorber}$ and $E_{substrate}$ at which recrystallization or contamination on the reticle front face or rear face occurs lithographically are known, the maximum number of semiconductor wafers $Z_{wafer\_absorber}$ and $Z_{wafer\_substrate}$ which can be exposed can be stated. Since $E_{wafer}$ is a dynamic control variable for the exposure process, dynamic control variables for defect inspections of the reticle front face and rear face are likewise $Z_{wafer\_absorber}$ and $Z_{wafer\_substrate}$, assuming that $E_{absorber}$ and $E_{substrate}$ are predetermined. If noticeable pellicle cloudiness occurs, for example, as a result of a change in the transmission characteristics of the polymer or as a result of surface contamination, then this has the same effect as an offset on the dose value $E_{wafer}$, thus resulting in lower values for $Z_{wafer\_absorber}$ and $Z_{wafer\_substrate}$.

The mechanical load on the reticle is recorded by recording the number of reticle movements within and outside the exposure system. Macro monitoring is carried out, if a predetermined counter limit is exceeded. If this monitoring limit or the monitoring limit calculated for the energy reticle load is not exceeded, macro monitoring and a defect inspection are carried out when a predetermined time limit is exceeded. Any pellicle cloudiness which occurs is also generally noticed at an early stage during macro monitoring.

If different threshold dose values are used to resolve crystal formations on the front face 9 and rear face 10 of the reticle, for example, by encapsulation of the reticle on one side or by different subsequent treatment of the surfaces, both threshold dose values are used for determination of the maximum exposure of the semiconductor wafers 1, in order to subject the reticle to a defect inspection.

The method according to the invention will be explained in more detail in the following text with reference to a number of examples, illustrating different individual contributions to $E_{absorber}$ and $E_{substrate}$ for different exposure conditions.

TABLE 1

| Wafer diameter [mm] | Wavelength | Reduction factor of the projection lens | Projection lens transmission | Number of shots/wafers | Tool factor |
|---|---|---|---|---|---|
| 300 | 365 nm i-line | 4 | 0.5 | 100 | 13 |
| 300 | 248 nm DUV | 4 | 0.35 | 100 | 18 |
| 300 | 193 nm DUV | 4 | 0.1 | 100 | 63 |

The number of image fields (also referred to as shots) $S_{wafer}$ to be exposed on each semiconductor wafer is obtained from the image field size and the size of the semiconductor wafer to be exposed. A typical value of about 100 shots per semiconductor wafer 1 is obtained for a semiconductor wafer with a diameter of 300 mm. Modern exposure systems typically have a reduction ratio of 1:4, thus resulting in a value of 4 for the reduction scale M.

In a first example, the structure transfer of an interconnect plane of a reticle into the resist layer 3 on the semiconductor wafer 3 is considered in an exposure system with a wavelength of 193 nm. This results in the following values. The radiant transmittance of the projection lens 4 of the exposure system for a wavelength of 193 nm is $T_{projection\ lens}=0.1$. The variable $S_{wafer}/(M^2 * T_{projection\ lens})$ is also referred to as the tool factor. The tool factors for a 300 mm semiconductor wafer are shown for various wavelengths (365 nm i-line, 248 nm DUV and 193 nm DUV) in Table 1.

Typical values around $T_{absorber}=0.06$ are indicated for the radiant transmittance of the absorber layer 6 at 193 nm. The substrate transmission of the quartz glass 7 of the reticle at this wavelength is $T_{substrate}=0.86$, and that for the transmittance of the pellicle 5 is $T_{pellice}=0.95$.

TABLE 2

| Reticle type | Wavelength [nm] | Substrate transmission $T_{substrate}$ | Absorber transmission $T_{absorber}$ (Cr/MoSi) | Mean pellicle transmission $T_{pellicle}$ |
|---|---|---|---|---|
| COG | 365 i-line | 0.92 | 0.02 | 0.98 |
| COG | 248 DUV | 0.85 | 0.005 | 0.98 |
| HPSM | 248 DUV | 0.85 | 0.08 | 0.98 |
| HPSM | 193 DUV | 0.92 | 0.03 | 0.99 |
| APSM | 248 DUV | 0.85 | 0.08 | 0.98 |
| APSM | 193 DUV | 0.92 | 0.03 | 0.99 |

Table 2 shows the associated radiant transmittance values for different wavelengths and for various mask types (i.e., chromium on glass COG, half-tone phase mask HPSM, alternating phase mask APSM).

A mean dose at the location of the resist layer 3 for a reticle on an interconnect plane with a CFR value of 0.46 of 26 mJ/cm² is required in order to transfer the structures into the resist at the wafer location in accordance with the specification.

With a limit value of 4 kJ/cm² for the front face 9 and for the rear face 10 of the reticle, the reticle is examined, at the latest, before 4500 exposed semiconductor wafers 1 on the rear face 10 by macro inspection, and, at the latest before 10600 exposed semiconductor wafers 1 on the front face 9, for a defect inspection relating to crystal formations.

Purging of the projection lens reticle area within the exposure system, for example, with $N_2$, reduces the formation of ammonium sulfate and tricyanic acid crystals. Such processes such often include surface dehydration in the reaction mechanism. Purging of the optical system of an exposure system with, for example, $N_2$ can often reduce the progress of processes such as these, which leads to an increase in the values for $Z_{wafer\_absorber}$ and $Z_{wafer\_substrate}$.

This can be taken into account by a correction factor K, which is specific for the exposure system. Since modern exposure systems are generally equipped with such purging, the maximum values $Z_{wafer\_absorber}$ and $Z_{wafer\_substrate}$ may, from experience, be increased by the correction factor K=1.3, thus resulting in a defect inspection before 5800 exposed semiconductor wafers 1 for the rear face 10 of the reticle, and before 13800 exposed semiconductor wafers 1 for the front face 9 of the reticle.

The appropriate preventive monitoring is carried out in each case at a quarter of the maximum value of $Z_{wafer\_absorber}$ and $Z_{wafer\_substrate}$, since the maximum values represent possible failure of the reticle, and must not be reached without a monitoring step.

A further example is intended to analyze the situation of a structure transfer of an implantation level on an exposure system with a wavelength of 365 nm. This results in the following values for a reduction projection lens for which M=4, and with a 100 shots on a 300 mm semiconductor wafer. The radiant transmittance of the projection lens for this wavelength is $T_{projection\ lens}=0.6$.

TABLE 3

| Wavelength [nm] | Plane type | Clear field ratio CFR | Mean wafer dose [mJ/cm²] | Max. number of wafers $Z_{wafer\_absorber}$ | Max. number of wafers $Z_{wafer\_reticle}$ |
|---|---|---|---|---|---|
| 248 | Interconnects | 0.57 | 22 | 2800 | 1400 |
| 193 | Interconnects | 0.57 | 21 | 900 | 500 |

TABLE 3-continued

| Wavelength [nm] | Plane type | Clear field ratio CFR | Mean wafer dose [mJ/cm$^2$] | Max. number of wafers $Z_{wafer\_absorber}$ | Max. number of wafers $Z_{wafer\_reticle}$ |
|---|---|---|---|---|---|
| 365 | Implant | 0.04 | 1400 | 64000 | 3200 |
| 365 | Contact hole | 0.17 | 3550 | 2500 | 400 |
| 365 | Contact hole | 0.02 | 360 | 6500 | 500 |
| 365 | Interconnects | 0.2 | 1090 | 6200 | 1200 |
| 365 | Implant | 0.02 | 1010 | 198200 | 7200 |
| 365 | Implant | 0.11 | 1030 | 18700 | 2200 |
| 365 | Implant | 0.72 | 2200 | 300 | 200 |
| 365 | Implant | 0.77 | 2620 | 200 | 100 |
| 365 | Implant | 0.1 | 1520 | 14800 | 1600 |
| 365 | Implant | 0.16 | 2420 | 4200 | 700 |

The radiant transmittance of the absorber layer 6 of the reticle is likewise set to 0.06. The transmittance of the reticle substrate 7, which may, for example, be formed of quartz glass is about 0.92 at this wavelength, and the transmittance $T_{pellicle}$ of the pellicle 5 is 0.97.

With a CFR value of 0.11 and a mean dose of 105 mJ/cm$^2$ and a limit value of 5 kJ/cm$^2$ for $E_{absorber}$ and $E_{substrate}$, the rear face 10 of the reticle is subject to a macro inspection before 4300 exposed semiconductor wafers 1, and the front face 9 of the reticle is subject to a defect inspection before 28300 exposed semiconductor wafers 1.

For the same reason, the corresponding monitoring is also carried out preventively in this case at a quarter of the maximum value, with the reticle being subject to a cleaning step, if required.

The macro inspection is also based on the number of reticle movements. When a maximum number for $Z_{wafer\_absorber}$ and $Z_{wafer\_substrate}$ of 800 for critical level in the first example, and 3000 for non-critical levels (as in the second example) is reached, then the reticles are subject to a macro inspection for possible defects larger than 10 µm. At the same time, the reticle is examined for possible contamination or polymer changes, which are evident as pellicle cloudiness.

Further examples for different wavelengths and different types of layer levels (with different CFR values) are shown in Table 3. Highly different values are obtained for the maximum number for $Z_{wafer\_absorber}$ and $Z_{wafer\_substrate}$, and this once again underlines the necessity for a dynamic monitoring method.

In summary, the method according to the invention includes preventively macro monitoring and defect inspecting the reticle with regard to mechanical loading, including particle deposits or electrostatically induced damage, and energy load, including the changes to the reticle material and surface characteristics. Different surface distributions of the absorber layer as well as characteristics of the exposure system, such as N$_2$ purging of the projection lens/reticle area in order to reduce contamination and recrystallization on optically active surfaces, can be considered.

During the manufacturing process, this preventive monitoring ensures that the faults which are present on the reticle are too small for the lithographic process and thus have no effect. When larger faults occur, such as particles which cannot be removed or crystal formation with a size above the resolution limit of the exposure system, the reticles are sent for cleaning in good time.

For example, the different radiant transmittance of the reduction optics at the wavelengths used for the structure transfer can lead to a different radiation load on the reticles. With a relatively small image field, which is dependent on the product to be produced, parts of the reticle are covered by mechanical shutters, and are thus protected against the influence of the radiation.

At the same time, this makes optimum use of the capacity of the reticle monitoring systems. Furthermore, different material characteristics of the reticle and of the pellicle as well as the extent to which the area of the reticle absorber layer is covered are included in the analyses. Overall, this complex analysis results in dynamic monitoring limits which are specific for each reticle, so that each reticle can be monitored at the correct time.

If a reticle is being used and the calculated energetic monitoring limit has not, however, been reached, then this reticle is set for monitoring when a predetermined time limit has been reached. This makes it possible to remove dirt, for example resulting from handling of the reticle, and to identify long-term effects preventively, and to send the reticle for cleaning.

While the invention has been described in detail and with reference to specific embodiments thereof, it will be apparent to one skilled in the art that various changes and modifications can be made therein without departing from the spirit and scope thereof. Accordingly, it is intended that the present invention covers the modifications and variations of this invention provided they come within the scope of the appended claims and their equivalents.

LIST OF REFERENCE SYMBOLS

1 Semiconductor wafer
2 Exposure field
3 Resist layer
4 Projection lens
5 Pellicle
6 Absorber layer
7 Reticle substrate
8 Antireflection layer
9 Front face
10 Rear face
11 First beam path
12 Second beam path

What is claimed:

1. A method for dynamically monitoring a reticle, which is used for the photolithographic structuring of a semiconductor wafer in a projection apparatus, comprising:

providing a reticle, the reticle having a pellicle, a reticle substrate, and an absorber layer, the absorber layer including absorbent elements designed in accordance with a circuit pattern;

photolithographic structuring of layers of semiconductor wafers in a projection apparatus with the reticle using electromagnetic radiation at a predetermined wavelength;

determining a number of reticle movements within and outside the projection apparatus;

determining a time duration of reticle use;

calculating a monitoring value from the number of reticle movements and from the time duration of reticle use;

determining a dose value of the electromagnetic radiation at a location of the layer for each exposure;

recording characteristics of a projection lens of the projection apparatus for the predetermined wavelength for each exposure;

determining a clear field ratio of the reticle;

determining an illuminated area of the semiconductor wafer;

determining a radiant transmittance of the pellicle for the predetermined wavelength;

determining a radiant transmittance of the absorber layer for the predetermined wavelength;

determining a radiant transmittance of the reticle substrate for the predetermined wavelength;

calculating a maximum number of wafer exposures from the monitoring value, from the dose value, from the characteristics of the projection lens, from the clear field ratio, from the illuminated area, from the radiant transmittance of the pellicle, from the radiant transmittance of the absorber layer, and from the radiant transmittance of the reticle substrate; and dynamically monitoring the reticle used in the photolithographic structuring of layers of the semiconductor wafers in accordance with the calculated maximum number of wafer exposures.

2. The method as claimed in claim 1, wherein the monitoring includes macro inspecting and defect inspecting the pellicle subject to an optical inspection during the macro monitoring for verifying cloudiness of the pellicle.

3. The method as claimed in claim 1, wherein the maximum number of wafer exposures for the reticle substrate and for the absorber layer of the reticle are determined separately, and the time for reticle monitoring is determined from the lower of the two values.

4. The method as claimed in claim 1, wherein a correction factor is applied to locally different clear field ratios at different positions of the reticle.

5. The method as claimed in claim 1, wherein the maximum number of wafer exposures in the presence of measures, which prevent contamination, is calculated using a correction factor.

6. The method as claimed in claim 5, wherein the measures which prevent contamination include purging with an inert gas.

7. The method as claimed in claim 1, wherein, if a front face and a rear face of the reticle have different chemical/physical surface characteristics, different threshold dose values at different exposure wavelengths are used for surface changes, the surface changes being used to determine the maximum wafer exposure in order to inspect the respective reticle surface.

8. The method as claimed in claim 1, wherein the reticle is one of a COG mask, a half-tone phase mask, an alternating phase-shift mask, a stencil mask, or an other photolithographic mask.

9. The method as claimed in claim 1, wherein the characteristics of the projection lens are determined by a radiant transmittance at the predetermined wavelength and by a reduction factor for mapping.

10. The method as claimed in claim 1, wherein photolithographic structuring of a layer includes exposing a resist layer, the dose value of the exposure being determined by the specifications for the resist.

11. The method as claimed in claim 1, wherein the monitoring of the reticle is carried out for a predetermined fraction of the maximum number of wafer exposures, the fraction being different for critical and non-critical levels.

12. The method as claimed in claim 6, wherein the inert gas is one of nitrogen or argon.

* * * * *